(12) United States Patent
Piergallini et al.

(10) Patent No.: US 10,687,926 B2
(45) Date of Patent: Jun. 23, 2020

(54) PHOTOTHERAPY DEVICES AND METHODS

(71) Applicant: KLOX Technologies Inc., Laval (CA)

(72) Inventors: Remigio Piergallini, Grottammare Ascoli Piceno (IT); Nikolaos Loupis, Athens (GR); Lise Hébert, Montreal (CA)

(73) Assignee: KLOX TECHNOLOGIES INC., Laval, Quebec (CA)

( * ) Notice: Subject to any disclaimer, the term of this patent is extended or adjusted under 35 U.S.C. 154(b) by 0 days.

(21) Appl. No.: 15/703,141

(22) Filed: Sep. 13, 2017

(65) Prior Publication Data
US 2018/0071066 A1 Mar. 15, 2018

Related U.S. Application Data

(62) Division of application No. 13/797,277, filed on Mar. 12, 2013, now Pat. No. 9,795,466.
(Continued)

(51) Int. Cl.
*A61N 5/06* (2006.01)
*A61C 13/15* (2006.01)
*A61C 1/08* (2006.01)

(52) U.S. Cl.
CPC ............ *A61C 19/004* (2013.01); *A61C 1/088* (2013.01); *A61N 5/062* (2013.01); *A61N 5/0603* (2013.01);
(Continued)

(58) Field of Classification Search
CPC .................... A61N 5/06; A61N 5/0603; A61N 2005/0605; A61N 2005/0606; A61N 2005/0607; A61N 2005/0608; A61N 2005/0609; A61N 2005/061; A61N 2005/0611; A61N 2005/0613; A61N 2005/062; A61N 2005/0624; A61N 2005/063; A61N 2005/0635; A61N 2005/0643; A61N 2005/0644;
(Continued)

(56) References Cited

U.S. PATENT DOCUMENTS

| 4,666,406 | A | 5/1987 | Kanca, III |
| 5,267,995 | A | 12/1993 | Doiron et al. |

(Continued)

FOREIGN PATENT DOCUMENTS

| CN | 1968983 A | 5/2007 |
| CN | 101163453 A | 4/2008 |

(Continued)

OTHER PUBLICATIONS

Machine translation provided for JP 0340964.
(Continued)

*Primary Examiner* — Ahmed M Farah
(74) *Attorney, Agent, or Firm* — BCF LLP

(57) ABSTRACT

The present disclosure relates to a phototherapy device that can deliver light to tissues to activate photoactive agents that have been applied to the tissues or that are included within a fiber optic tip member of the device which may be coupled to a light source using a sleeve. The present disclosure also relates to methods of phototherapy using the phototherapy device such as anti-bactericidal treatment, anti-fungal treatment, anti-parasitic treatment, anti-viral treatment.

1 Claim, 8 Drawing Sheets

Related U.S. Application Data

(60) Provisional application No. 61/653,288, filed on May 30, 2012.

(52) U.S. Cl.
CPC ...... *A61N 5/0624* (2013.01); *A61N 2005/063* (2013.01); *A61N 2005/0606* (2013.01); *A61N 2005/0643* (2013.01); *A61N 2005/0644* (2013.01); *A61N 2005/0651* (2013.01); *A61N 2005/0654* (2013.01)

(58) Field of Classification Search
CPC .............. A61N 2005/065; A61B 18/18; A61B 2018/1807; A61B 2018/1861; A61B 18/20; A61B 2018/2015; A61B 18/22; A61B 2018/2205; A61B 2018/2244; A61B 2018/2255; A61B 2018/2261; A61C 1/0046; A61C 1/0053; A61C 1/08; A61C 1/088; A61C 19/002; A61C 19/003; A61C 19/004
USPC ........ 607/88–90, 93; 606/13, 16, 17; 433/29
See application file for complete search history.

(56) References Cited

U.S. PATENT DOCUMENTS

| | | | |
|---|---|---|---|
| 5,420,768 A * | 5/1995 | Kennedy | A61C 19/004 362/109 |
| 5,759,032 A | 6/1998 | Bartel | |
| 5,968,033 A | 10/1999 | Fuller et al. | |
| 6,004,315 A | 12/1999 | Dumont | |
| 6,019,605 A | 2/2000 | Myers | |
| 6,133,488 A * | 10/2000 | Hirai | C07C 29/78 568/818 |
| 6,208,788 B1 * | 3/2001 | Nosov | A61C 19/004 362/554 |
| 6,270,492 B1 | 8/2001 | Sinofsky | |
| 6,810,184 B2 | 10/2004 | Skutnik | |
| 6,957,907 B2 * | 10/2005 | Fischer | A61B 5/0088 362/16 |
| 7,074,040 B2 | 7/2006 | Kanca | |
| 7,182,597 B2 * | 2/2007 | Gill | A61C 19/004 362/800 |
| 7,609,927 B2 | 10/2009 | Gowda et al. | |
| 7,645,056 B1 | 1/2010 | Mills et al. | |
| 7,950,396 B2 * | 5/2011 | Rose | A61N 5/0603 128/898 |
| 9,808,646 B2 * | 11/2017 | Piergallini | A46B 15/0034 |
| 2002/0028041 A1 | 3/2002 | Easley | |
| 2004/0214131 A1 | 10/2004 | Fischer et al. | |
| 2005/0026103 A1 | 2/2005 | Wasylucha | |
| 2005/0107853 A1 * | 5/2005 | Krespi | A61B 18/18 607/89 |
| 2005/0221250 A1 | 10/2005 | Kanca | |
| 2005/0260375 A1 | 11/2005 | Clarke et al. | |
| 2006/0115783 A1 | 6/2006 | Mclaren | |
| 2008/0060148 A1 | 3/2008 | Pinyayev | |
| 2008/0154317 A1 | 6/2008 | Loebel | |
| 2009/0003785 A1 | 1/2009 | Parris et al. | |
| 2009/0081605 A1 | 3/2009 | Hay et al. | |
| 2010/0330523 A1 | 12/2010 | Kert | |
| 2011/0123958 A1 | 5/2011 | Piergallini et al. | |
| 2011/0264026 A1 | 10/2011 | Rajagopalan | |
| 2011/0296643 A1 | 12/2011 | Shepherd et al. | |
| 2013/0109804 A1 * | 5/2013 | Kusaka | C08F 290/067 524/590 |
| 2013/0289672 A1 * | 10/2013 | Hakomori | A61B 18/24 607/89 |
| 2013/0296287 A1 * | 11/2013 | Charbit | A61N 5/062 514/186 |

FOREIGN PATENT DOCUMENTS

| | | |
|---|---|---|
| CN | 101686851 A | 3/2010 |
| DE | 102010045845 A1 | 7/2011 |
| EP | 0292621 A1 | 11/1988 |
| EP | 1765898 B1 | 8/2010 |
| EP | 2012877 B1 | 8/2012 |
| JP | 62160918 U | 10/1987 |
| JP | 63182706 U | 11/1988 |
| JP | 0340964 U | 4/1991 |
| JP | 05278752 A | 10/1993 |
| JP | 2008-537313 A | 9/2008 |
| JP | 2009119118 A | 6/2009 |
| RU | 2106887 C1 | 3/1998 |
| WO | 2011058448 A2 | 5/2001 |
| WO | 2006115761 A1 | 11/2006 |
| WO | 2007127894 A2 | 4/2007 |
| WO | 2008051918 A2 | 5/2008 |

OTHER PUBLICATIONS

English Abstract provided for JP 05278752.
Machine translation provided for JP 62160918.
Machine translation provided for JP 63182706.
English Abstract provided for JP 2009119118.
English abstract for CN1968983A.

* cited by examiner

PHOTOTHERAPY DEVICES AND METHODS

CROSS-REFERENCE TO RELATED APPLICATIONS

This application is a divisional of U.S. application Ser. No. 13/797,277, filed on Mar. 12, 2013, which claims the benefit of U.S. Provisional Application No. 61/653,288, filed on May 30, 2012. The specifications of each of the above-referenced applications are hereby incorporated by reference in their entirety.

BACKGROUND OF THE DISCLOSURE

Phototherapy has recently been recognized as having a wide range of applications in both the medical, cosmetic and dental fields for use in surgeries, therapies and examinations. Phototherapy is commonly used as a means of disinfecting target sites. Phototherapeutic techniques have been applied to kill bacteria in the oral cavity and for whitening teeth. Phototherapy is also used to promote wound healing, skin rejuvenation and to treat skin conditions such as acne. These techniques typically rely on the use of laser light sources. Lasers, however, can be very dangerous, particularly in clinical settings, and are typically expensive, large, cumbersome and complicated to use. Accordingly, there is a need for an improved phototherapy device.

SUMMARY OF THE DISCLOSURE

The present disclosure provides devices and methods useful in phototherapy including phototherapy device members and phototherapy kits that can utilize any light source, not necessarily lasers, but still provide effective treatment. The use of common clinical light sources such as LEDs or halogen bulbs may be more desirable for phototherapy than lasers due to the cost and other disadvantages associated with lasers. Thereby the phototherapy devices, device members, kits and methods of the present disclosure may simplify, complement and/or improve phototherapy regimens, such as for periodontal treatment, wound healing, collagen modulation, anti-bactericidal treatment, anti-fungal treatment, anti-parasitic treatment, anti-viral treatment, or anti-inflammatory treatment.

In certain embodiments, the present disclosure relates to a phototherapy device that can deliver light to the periodontal regions of the mouth to activate photoactive reagents that have been applied in periodontal pockets, e.g. between the gum and the tooth. The phototherapy device may comprise a fiber optic tip suitable for delivering light from a light source, such as a light emitting diode (LED), to periodontal regions of the mouth. The tip may be coupled to the light source using a sleeve that may help to maintain optical alignment. The present disclosure also relates to methods of treating and preventing periodontal disease using the phototherapy device to kill bacteria in a periodontal treatment region.

For purposes of clarity, and not by way of limitation, the devices, kits and methods of the present disclosure are described herein in the context of providing phototherapy for treatment or prevention of periodontal disease. However, it will be appreciated that the principles described herein may be adapted to a wide range of applications, such as for example in post extractive sockets, endodontic treatment in dental root canals, teeth whitening treatment, wound healing, key hole surgery/treatment or any antimicrobial or therapeutic application in hard to reach places of the body where a fiber optic may be useful. Uses for devices, methods and kits of the present disclosure also include for collagen modulation, anti-bactericidal treatment, anti-fungal treatment, anti-parasitic treatment, anti-viral treatment, or anti-inflammatory treatment. For example, the principles of this disclosure may be applied to phototherapeutic antibacterial treatment or tooth whitening between teeth. In addition, the principles may be applied to phototherapeutics in connection with orthodontics. More generally, the devices and methods described herein may be employed in any phototherapeutic treatment that requires the application of focused light, and in some cases, the application of light in generally closed and hard to reach sites of the mouth or other parts of the body. Accordingly, the devices, kits and methods disclosed herein may be performed instead of or in addition to conventional treatment methods, including subgingival debridement, supergingival debridement, scaling/root planning, wound healing, skin disorder treatment, topical and systemic treatments.

One aspect of the present disclosure provides a phototherapeutic device member. In some embodiments, the phototherapeutic device member comprises a flexible fiber optic tip member and an elastic tubular connector sleeve for mechanically coupling the flexible tip member to a light source. The flexible fiber optic tip member functions as a waveguide and transmits light along its length. The flexible fiber optic tip member may have a polymer core for transmitting light. The flexible fiber optic tip member may be made of any suitable material which can transmit light and has appropriate optical properties, such as a glass. The flexible fiber optic tip member can include a proximal end and a distal end, wherein the diameter of the proximal end is greater than the diameter of the distal end, and wherein the proximal end is curved to cause light entering the flexible tip member through the proximal end to converge. The elastic tubular connecting sleeve may include a proximal end having an opening and a distal end having an opening, the proximal end configured to be stretched and mechanically coupled to the light source. In use, the flexible fiber optic tip may be partially disposed within the elastic tubular connecting sleeve such that the distal end of the flexible fiber optic tip member extends distally through the opening in the distal end of the sleeve, and the proximal end of the flexible fiber optic tip member is disposed within the sleeve and between the proximal and distal ends of the sleeve, thereby positioning the flexible fiber optic tip member near the light source. The sleeve is configured to receive the flexible fiber optic tip such that the distal end of the flexible fiber optic tip member extends distally through the opening in the distal end of the sleeve, and the proximal end of the flexible fiber optic tip member is disposed within the sleeve and between the proximal and distal ends of the sleeve, thereby positioning the flexible fiber optic tip member near the light source.

The flexible fiber optic tip may be unitarily formed. The flexible fiber optic tip may be formed by moulding. Optionally, the flexible fiber optic tip is cut from a single block of polymer material. In some embodiments, the flexible fiber optic tip member has a rough surface formed such as by grating. The flexible fiber optic tip member may include a rough outer surface configured to allow a portion of light transmitted through the core to diffuse out through the outer surface. The flexible fiber optic tip can include an optical axis extending through the center of the polymer core from the proximal end to the distal end, and wherein light passing through the tip member travels along at least a portion of the optical axis. The polymer core of the flexible fiber optic tip may comprise polycarbonate or polymethylmethacrylate.

The flexible fiber optic tip may further comprise a photoactive agent which can absorb and emit light.

In some embodiments, an interior surface of the elastic tubular connector sleeve includes a plurality of ribs extending radially inwards (circumferentially) and configured to grip the light source or a catheter. The elastic tubular connector sleeve can be stretched around the light source or catheter and held in place by the ribs. In certain embodiments, the flexible fiber optic tip member is removable from the elastic tubular connector sleeve.

In some embodiments, a proximal region of the flexible fiber optic tip member is substantially conical having a base along the proximal end. The proximal end of the flexible fiber optic tip member may be convex shaped relative to the proximal portion of the flexible fiber optic tip member. A distal region of the tip member may be substantially cylindrical. The length from the proximal end to a distal end of the flexible fiber optic tip member is between about 10 mm and about 30 mm. The length may be much longer than this if a catheter is used. In which case the length of the flexible fiber optic tip member will be as long as the length of the catheter. The diameter at the distal end of the flexible fiber optic tip member is optionally between about 500 micron and about 1500 micron. Further, the diameter can vary along the length of the flexible fiber optic tip member. The diameter of the distal end of the flexible fiber optic tip members can vary according to the use. In certain embodiments, the distal end of the flexible fiber optic tip member may comprise a plurality of bristles, e.g. like brush. This may be useful in applications where debridement may be useful such as cleaning teeth, cleaning wounds, cleaning skin and the like.

In some embodiments, the light source to which the flexible fiber optic tip is coupled includes one or more light emitting diodes. Alternatively, the light source may include a halogen lamp. In some embodiments, the flexible fiber optic tip may be coupled to an end of a catheter.

A second aspect of the present disclosure, provides a device for phototherapy. In some embodiments, the device comprises a light source, a probe member having a flexible fiber optic tip member and an elastic tubular connector sleeve for mechanically coupling the probe member to the light source. The proximal end of the flexible fiber optic tip member may be curved to cause light entering the tip member through the proximal end to converge. The proximal end of the sleeve may be configured to be stretched and mechanically coupled to the light source. Optionally, the tip member is partially disposed within the sleeve and extends distally through a distal opening of the sleeve. The device may be used for treating/preventing periodontitis, in which case a distal end of the flexible fiber optic tip member is sized and/or shaped to be received in periodontal pockets. The device may also be used for treating tissues in hard to reach places, internal tissues and cavities such as through key-hole surgery, in which case the proximal end of the sleeve may be configured to be stretched and mechanically coupled to an end of a catheter. In this case, the flexible fiber optic tip member may extend along the length of the catheter and be attached to a light source at a proximal end of the catheter. A further sleeve according to the present disclosure may be provided for attaching to the light source at the proximal end of the catheter.

The flexible fiber optic tip may be unitarily formed. The flexible fiber optic tip may be formed by moulding. Optionally, the flexible fiber optic tip is cut from a single block of polymer material. In some embodiments, the flexible fiber optic tip member is grated to generate a rough surface. The flexible fiber optic tip member may include a rough outer surface configured to allow a portion of light transmitted through the core to diffuse out through the outer surface. The flexible fiber optic tip can include an optical axis extending through the center of the polymer core from the proximal end to the distal end, and wherein light passing through the tip member travels along a portion of the optical axis. The polymer core of the flexible fiber optic tip may comprise polycarbonate or polymethylmethacrylate. The flexible fiber optic tip may further comprise a photoactive agent which can absorb light and emit as energy.

In some embodiments, an interior surface of the elastic tubular connector sleeve includes a plurality of ribs extending radially inwards (circumferentially) and configured to grip the light source. In certain embodiments, the flexible fiber optic tip member is removable from the sleeve.

In some embodiments, a proximal region of the flexible fiber optic tip member is substantially conical having a base along the proximal end. A distal region of the tip member may be substantially cylindrical. The length from the proximal end to a distal end of the flexible fiber optic tip member is between about 10 mm and about 30 mm. The length may be much longer than this if a catheter is used. In which case the length of the flexible fiber optic tip member will be as long as the length of the catheter. The diameter at the distal end of the flexible fiber optic tip member is optionally between about 500 micron and about 1500 micron. Further, the diameter can vary along the length of the flexible fiber optic tip member. The proximal end of the flexible fiber optic tip member may be convex shaped relative to the proximal portion of the flexible fiber optic tip member. Further, the diameter can vary along the length of the flexible fiber optic tip member. The diameter of the distal end of the flexible fiber optic tip members can vary according to the use. In certain embodiments, the distal end of the flexible fiber optic tip member may comprise a plurality of bristles, e.g. like brush. This may be useful in applications where debridement may be useful such as cleaning teeth, cleaning wounds, cleaning skin and the like.

In some embodiments, the device further comprises an actuating mechanism for moving at least the flexible fiber optic tip member relative to a treatment surface. For example, the actuating mechanism may further comprise a motor in communication with the flexible fiber optic tip member to move the flexible fiber optic tip member backwards and forwards across the treatment surface (substantially perpendicular to the optical axis), or to cause the flexible fiber optic tip member to vibrate.

In some embodiments, the light source to which the flexible fiber optic tip is coupled includes one or more light emitting diodes. Alternatively, the light source may include a halogen lamp. In some embodiments, the flexible fiber optic tip may be coupled to an end of a catheter.

Another aspect of the present disclosure provides a method =of treating and/or preventing periodontal disease. In some embodiments, the method comprises attaching to a light source having one or more light-emitting diodes a periodontal probe member, which comprises a flexible fiber optic tip member with a polymer or glass core for transmitting light, and an elastic tubular connector sleeve, for mechanically coupling the flexible tip member to a light source; introducing a composition comprising a photoactivating agent and oxygen-releasing agent into a periodontal treatment region; introducing the flexible fiber optic tip into the periodontal treatment region; and applying light through the flexible fiber optic tip member to activate the photoactivating agent in the periodontal treatment region. By "photoactivating agent" is meant a chemical compound which, when contacted by light irradiation, is capable of absorbing the light. The photoactivating agent readily undergoes photoexcitation and can then transfer its energy to other molecules or emit it as light. The terms "photoactivating agent", "photoactive agent" and "chromophore" are used herein interchangeably herein.

Another aspect of the present disclosure provides a method for treating wounds. In some embodiments, the method comprises attaching to a light source having one or more light-emitting diodes a probe member, which comprises a flexible fiber optic tip member with a polymer or glass core for transmitting light, and an elastic tubular connector sleeve, for mechanically coupling the flexible tip member to a light source or a catheter; introducing a composition comprising a photoactivating agent and oxygen-releasing agent into a treatment region; introducing the flexible fiber optic tip member into the treatment region; and applying light through the flexible fiber optic tip member to activate the photoactivating agent in the treatment region.

Another aspect of the present disclosure provides a method for antibacterial treatment of a tissue site. In some embodiments, the method comprises attaching to a light source having one or more light-emitting diodes a probe member, which comprises a flexible fiber optic tip member with a polymer or glass core for transmitting light, and an elastic tubular connector sleeve, for mechanically coupling the flexible tip member to a light source or a catheter; introducing a composition comprising a photoactivating agent and an oxygen-releasing agent into a the tissue site; introducing the flexible fiber optic tip member into the tissue site; and applying light through the flexible fiber optic tip member to activate the photoactivating agent in the tissue site. The flexible fiber optic tip may be unitarily formed, such as by moulding. Optionally, the flexible fiber optic tip is cut from a single block of polymer material. In some embodiments, the flexible fiber optic tip member is grated to generate a rough surface. The flexible fiber optic tip member may include a rough outer surface configured to allow a portion of light transmitted through the core to diffuse out through the outer surface. The flexible fiber optic tip can include an optical axis extending through the center of the polymer core from the proximal end to the distal end, and wherein light passing through the tip member travels along a portion of the optical axis. The polymer core of the flexible fiber optic tip may comprise polycarbonate or polymethylmethacrylate.

In some embodiments, an interior surface of the elastic tubular connector sleeve includes a plurality of ribs extending radially inwards (circumferentially) and configured to grip the light source or the catheter. In certain embodiments, the flexible fiber optic tip member is removable.

In some embodiments, a proximal region of the flexible fiber optic tip member is substantially conical having a base along the proximal end. The proximal end of the flexible fiber optic tip member may be convex shaped relative to the proximal portion of the flexible fiber optic tip member. A distal region of the tip member may be substantially cylindrical. The length from the proximal end to a distal end of the flexible fiber optic tip member is between about 10 mm and about 30 mm. The length may be much longer than this if a catheter is used. In which case the length of the flexible fiber optic tip member will be as long as the length of the catheter. The diameter at the distal end of the flexible fiber optic tip member is optionally between about 500 micron and about 1500 micron. Further, the diameter can vary along the length of the flexible fiber optic tip member. The diameter of the distal end of the flexible fiber optic tip members can vary according to the use. In certain embodiments, the distal end of the flexible fiber optic tip member may comprise a plurality of bristles, e.g. like brush. This may be useful in applications where debridement may be useful such as cleaning teeth, cleaning wounds, cleaning skin and the like.

The periodontal treatment region can be exposed to the light for a period of less than five minutes, such as between one minute and five minutes. The method may comprise exposing the periodontal treatment region to light for about 1-30 minutes, about 1-25 minutes, about 1-20 minutes, about 1-15 minutes, about 1-10 minutes. The method may be performed over several distinct periodontal treatment regions within the oral cavity. In such cases, each periodontal treatment region exposed to the light for a period of less than five minutes, such as between one minute and five minutes. The light may have a wavelength between about 400 nm and about 800 nm.

The composition may be introduced on a gingiva within the oral cavity, or a portion thereof. The composition may be introduced near at least one tooth, preferably on at least one tooth. The composition may be introduced between a gingiva and a tooth.

The oxygen-releasing agent may be hydrogen peroxide, carbamide peroxide or benzoyl peroxide. The photoactivating agent can be xanthene derivative dye, an azo dye, a biological stain or a carotenoid. Xanthene derivative dyes may be a fluorene dye, a fluorone dye or a rhodole dye. Optionally, the fluorene dye is a pyronine dye, such as pyronine Y or pyronine B, or a rhodamine dye, such as rhodamine B, rhodamine G or rhodamine WT. In some embodiments, the fluorone dye is fluorescein or a fluorescein derivative, such as phloxine B, rose Bengal, merbromine, eosin Y, eosin B or erthrosine B, preferably eosin Y. Optionally, the azo dye is methyl violet, neutral red, para red, amaranth, carmoisine, allura red AC, tartrazine, orange G, ponceau 4R, methyl red or murexide-ammonium purpurate. The biological stain may be saffranin O, basic fuchsin, acid fuchsin, 3,3' dihexylocarbocyanine iodide, carminic acid or indocyanine green. In some embodiments, the carotenoid is crocetin, a-crocin, zeaxanthine, lycopene, α-carotene, β-carotene, bixin, fucoxanthine, or a mixture of carotenoid compounds, such as saffron red powder, annatto extract or brown algae extract.

Another aspect of the present disclosure provides a method for phototherapeutic treatment, and which differs from the above method in that the flexible fiber optic tip member comprises a photoactive agent in the polymer or glass core. In some embodiments, the method comprises attaching to a light source having one or more light-emitting diodes a probe member, which comprises a flexible fiber optic tip member with a polymer or glass core for transmitting light and a photoactive agent, and an elastic tubular connector sleeve, for mechanically coupling the flexible tip member to a light source; introducing the flexible fiber optic tip member into the treatment region; and applying light through the flexible fiber optic tip member to activate the photoactive agent. When the photoactive agent is activated by the light, the flexible fiber optic tip member may fluoresce and or activate oxygen-releasing agents in the treatment region.

From a yet further aspect, there is provided a kit for phototherapy comprising a plurality of flexible fiber optic tip members, having a polymer or a glass core for transmitting light, the flexible tip member including a proximal end and a distal end, wherein the diameter of the proximal end is greater than the diameter of the distal end, and wherein the proximal end is curved to cause light entering the flexible tip member through the proximal end to converge; and an elastic tubular connector sleeve, for receiving at least a portion of one of the plurality of flexible fiber optic tip members and for mechanically coupling the flexible tip member to a light source, wherein the sleeve includes a proximal end having a first opening and a distal end having a second opening, the proximal end configured to be stretched and mechanically coupled to the light source.

The plurality of flexible fiber optic tip members may have different size and shape distal ends suitable for different applications. The plurality of flexible fiber optic tip members may include a photoactive agent in a polymer matrix. In certain embodiments, the kit further comprises a biophotonic composition comprising a photoactive agent. The composition may optionally include an oxygen-releasing agent.

DETAILED DESCRIPTION

The devices, kits and methods described herein will now be described with reference to certain illustrative embodiments. However, the disclosure is not to be limited to these illustrated embodiments which are provided merely for the purpose of describing the devices, kits and methods of the disclosure and are not to be understood as limiting in anyway.

Figure 1:
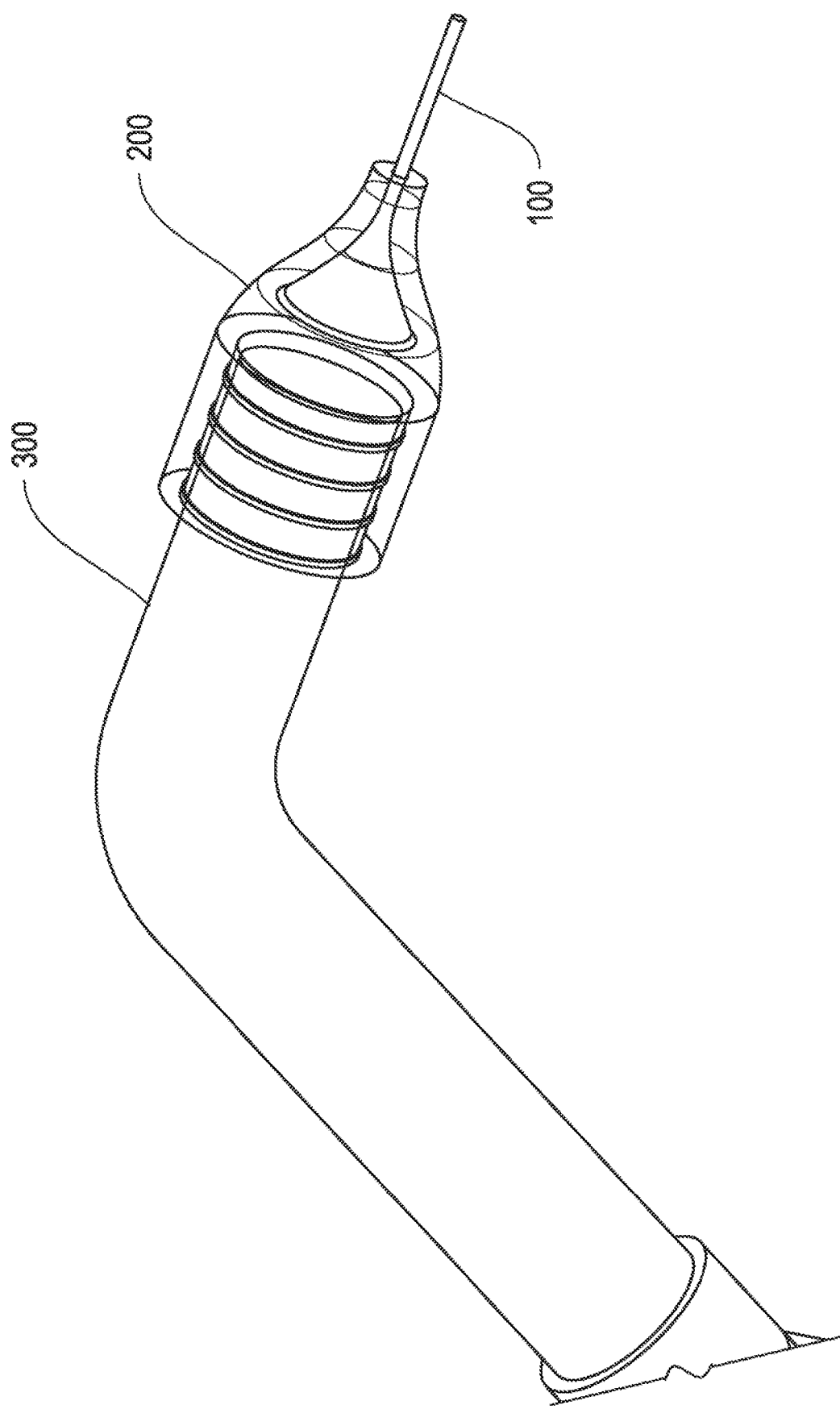
FIG. 1 depicts a phototherapeutic device, according to an illustrative embodiment of the present disclosure.

FIG. 1 depicts a phototherapeutic device in accordance with present disclosure. The phototherapeutic device comprises a flexible fiber optic tip member 100 coupled to a light source 300 with an elastic tubular connector sleeve 200. The flexible fiber optic tip member 100 will be discussed in greater detail in the descriptions of FIG. 2A-FIG. 2D. The elastic tubular connector sleeve will be discussed in greater detail in the descriptions of FIG. 3A and FIG. 3B.

The light source 300 may be any light source commonly found in a clinical setting, including, for example, light sources for photocuring. In some embodiments, the light source 300 comprises an elongated cable of a suitable length to permit a dental professional to work in a patient's mouth. Optionally, the light source 300 provides actinic light. In some embodiments, the light source 300 comprises light emitting diodes. Alternatively, the light source 300 may comprise a halogen lamp. In some embodiments, the light source 300 is configured to provide light at a wavelength that will activate a photoactivating agent. By "actinic light" is meant light energy emitted from a specific light source (e.g., lamp, LED, or laser) and capable of being absorbed by matter (e.g. the photoactivating agent). In a preferred embodiment, the actinic light is visible light. The light source 300 may provide visible light or ultraviolet light. In some embodiments, the light source 300 provides visible light having a wavelength between about 400 nm and about 800 nm. Furthermore, the light source 300 should have a suitable power density. Suitable power density for non-collimated light sources (LED, halogen or plasma lamps) are in the range from about 50 mW/cm$^2$ to about 200 mW/cm$^2$, about 30-150 mW/cm$^2$, A light beam from the light source 300 may travel from the light source to the proximal end 110 of a flexible fiber optic tip member 100 along the optical axis 190 to the distal end 120 for delivery to a periodontal treatment region. In certain embodiments, the light source 300 may emit a continuous beam of light or a pulsed beam of light.

The light source 300 may additionally include a control box attached to a flexible fiber optic waveguide to allow a dental professional to place the free end of the fiber optic waveguide in or near a patient's mouth. The control box of light source 300 may include a lamp, a transformer and a control board, which allows dental professionals to control variables such as light intensity and voltage. Light source 300 may be controlled by a foot pedal, which leaves the dental professionals hands free to operate the fiber optic waveguide in addition to any other dental tools. Light source 300 may also include a time-delay, such that the light transmitted through the fiber optic wave guide stays on after the foot pedal is released.

Figure 2A:
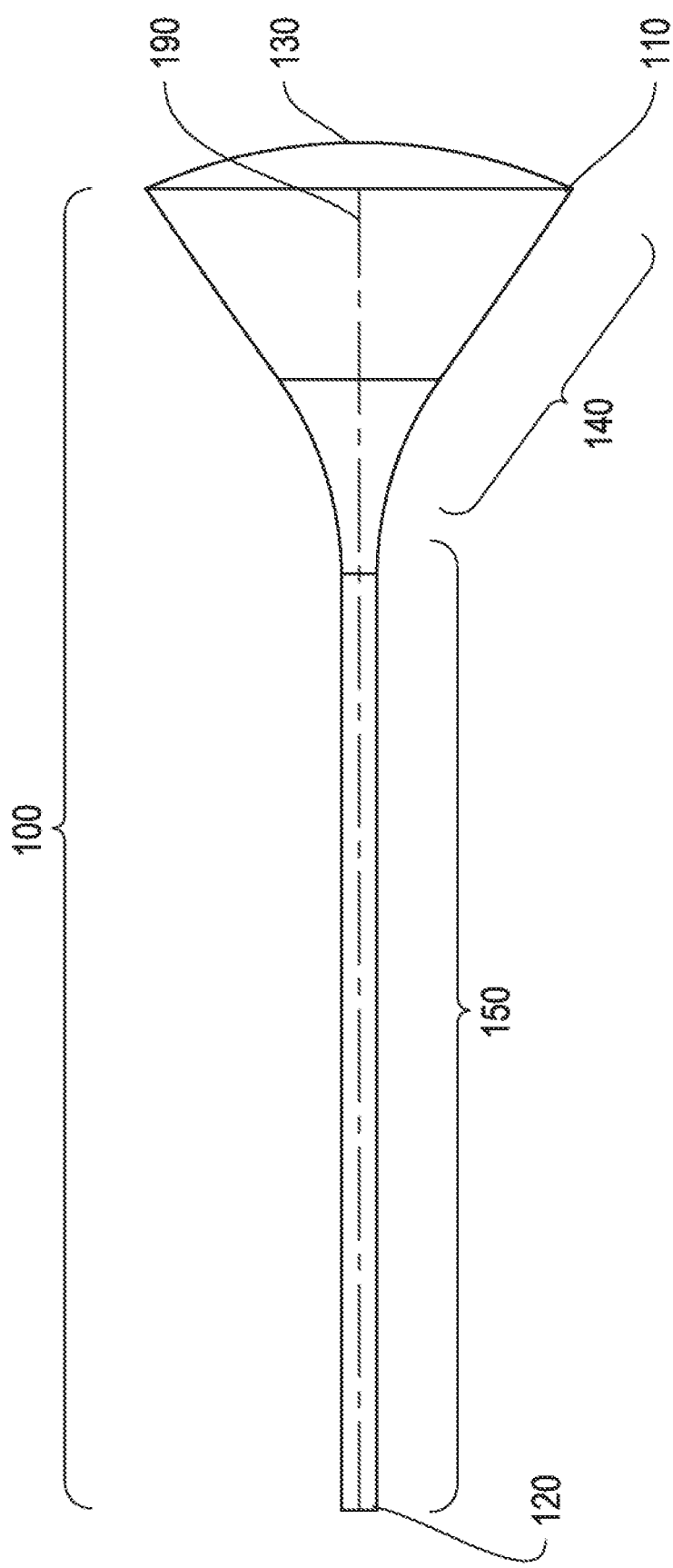
FIG. 2A depicts a flexible fiber optic tip member of the device of FIG. 1, according to an illustrative embodiment of the present disclosure.

FIG. 2A depicts a flexible fiber optic tip member 100 in accordance with the present disclosure. The flexible fiber optic tip member 100 has a polymer core along with a proximal end 110 configured for coupling to the light source 300 and a distal end 120 configured for insertion into a periodontal treatment region. The flexible fiber optic tip member 100 is configured to have a conical portion 140 proximal to a cylindrical portion 150. The conical portion 140 may have its base at the proximal end 110. The conical portion 140 will be configured to comprise a curved structure 130 to focus the light transmitted from the light source 300 into the cylindrical portion 150. Further, the flexible fiber optic tip member 100 is configured such at that light traverses through the polymer core along the optical axis 190.

Figure 2B:
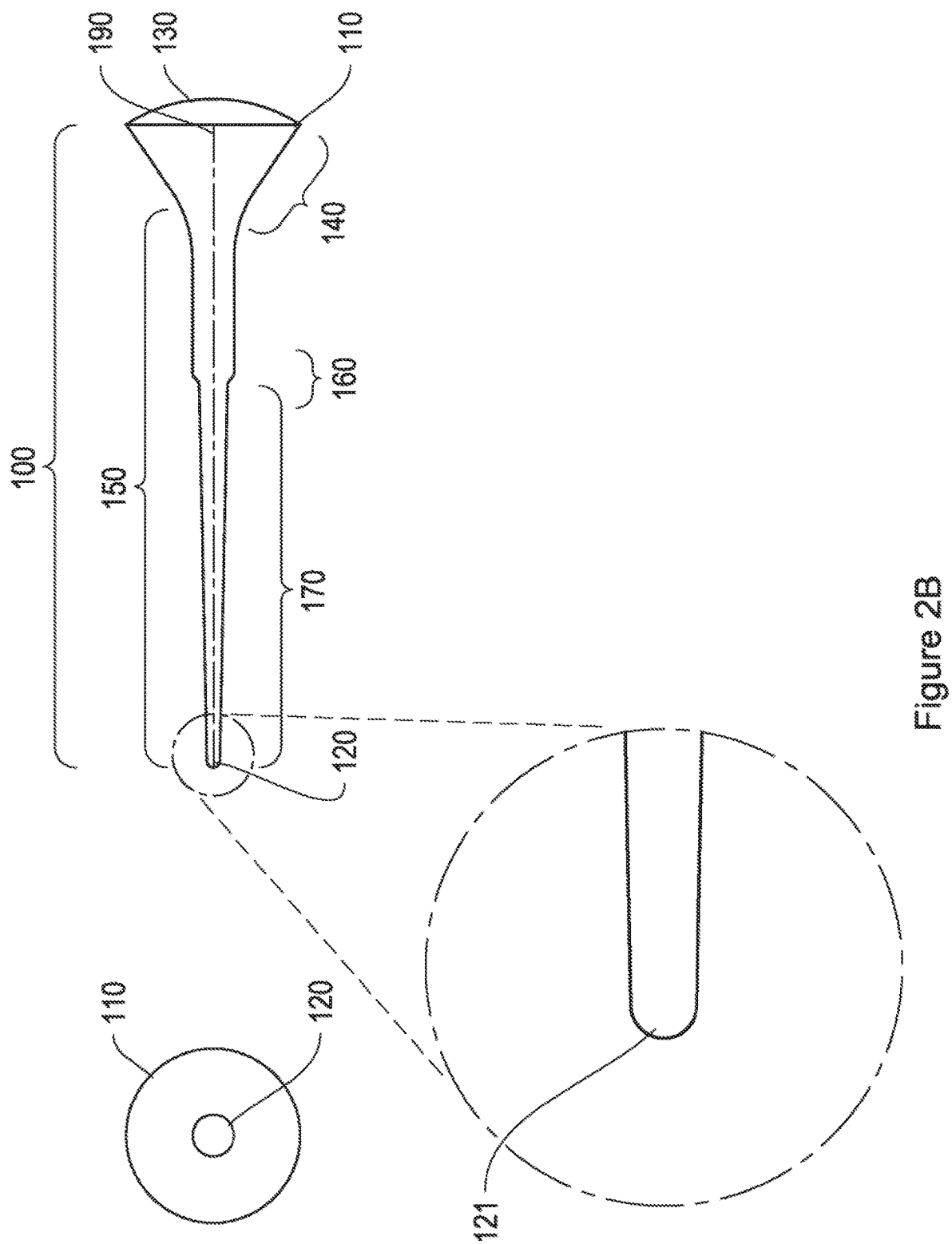
FIG. 2B-2C depict a flexible fiber optic tip member, of the device of FIG. 1, having a ridge, according to an illustrative embodiment of the present disclosure.

FIG. 2B depicts an additional flexible fiber optic tip member 100 in accordance with the present disclosure. The flexible fiber optic tip member 100 in FIG. 2B comprises a ridge feature 160, which may be configured to be disposed in the distal opening 250 of the elastic tubular connecting sleeve to help the flexible fiber optic tip member 100 in place near the light source 300. The flexible fiber optic tip member 100 has a polymer core along with a proximal end 110 configured for coupling to the light source 300 and a distal end 120 configured for insertion into a periodontal treatment region. The flexible fiber optic tip member 100 is configured to have a conical portion 140 proximal to a cylindrical portion 150. The cylindrical portion 150 can be configured to comprise a ridge 160 proximal to a flexible portion 170 which terminates at the distal end 120. The distal end 120 may comprise a rounded tip 121. The conical portion 140 may have its base at the proximal end 110. The conical portion 140 will be configured to comprise a curved structure 130 to focus the light transmitted from the light source 300 into the cylindrical portion 150. Further, the flexible fiber optic tip member 100 is configured such at that light traverses through the polymer core along the optical axis 190.

Figure 2C:
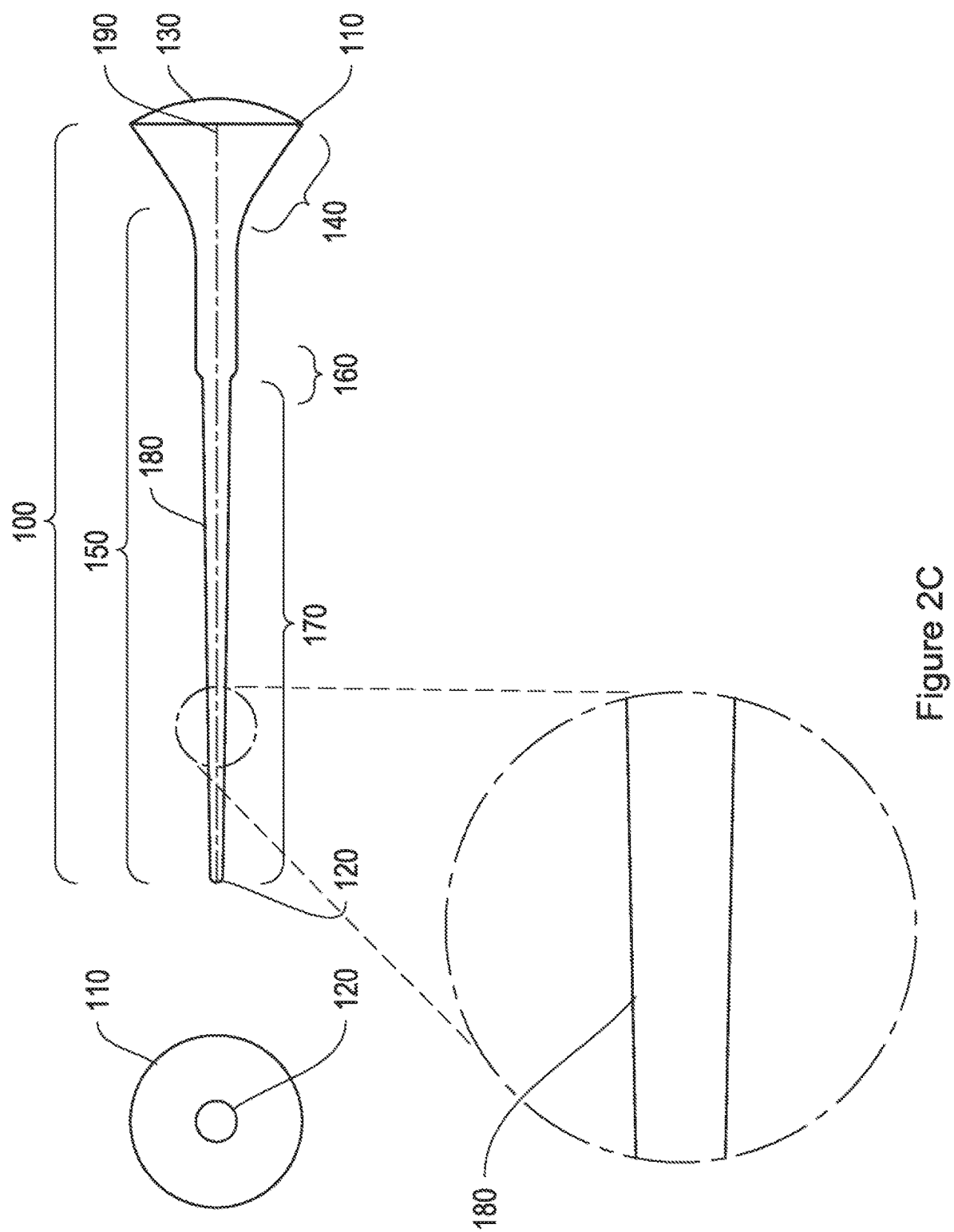

FIG. 2C depicts a further flexible fiber optic tip member 100 in accordance with the present disclosure. The flexible fiber optic tip member 100 in FIG. 2C comprises a ridge feature 160, which may be configured to be disposed in the distal opening 250 of the elastic tubular connecting sleeve to help the flexible fiber optic tip member 100 in place near the light source 300. Further the flexible fiber optic tip member 100 in FIG. 2C comprises a narrowing region 180, along which the diameter of the cylindrical portion 150 varies along the length of the cylindrical portion 150. The flexible fiber optic tip member 100 has a polymer core along with a proximal end 110 configured for coupling to the light source 300 and a distal end 120 configured for insertion into a periodontal treatment region. The flexible fiber optic tip member 100 is configured to have a conical portion 140 proximal to a cylindrical portion 150. The cylindrical portion 150 can be configured to comprise a ridge 160 proximal to a flexible portion 170 which terminates at the distal end 120. The flexible portion 170 may contain a narrowing region 180, wherein the diameter of the proximal end of the narrowing region 180 is greater than the diameter of the distal end for the narrowing region 180. The narrowing region 180 may traverse the entire length for the flexible portion 170, running from the ridge 160 to the distal end 120. The conical portion 140 may have its base at the proximal end 110. The conical portion 140 will be configured to comprise a curved structure 130 to focus the light transmitted from the light source 300 into the cylindrical portion 150. Further, the flexible fiber optic tip member 100 is configured such at that light traverses through the polymer core along the optical axis 190.

Figure 2D:
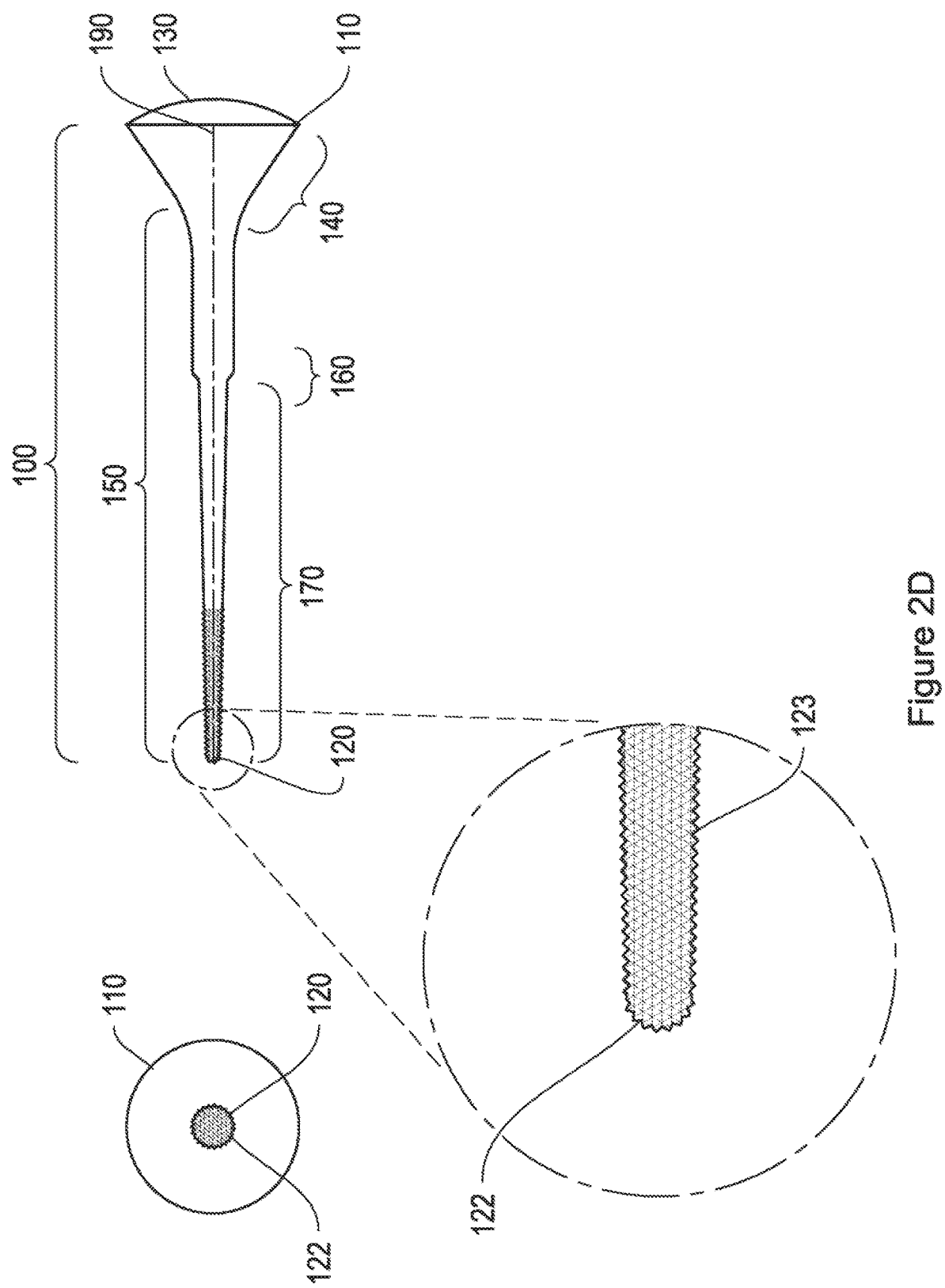
FIG. 2D depicts a flexible fiber optic tip member, of the device of FIG. 1, having a rough surface portion, according to an illustrative embodiment of the present disclosure.

FIG. 2D depicts another flexible fiber optic tip member 100 in accordance with the present disclosure. The flexible fiber optic tip member 100 in FIG. 2D comprises a rough outer surface 123 and a rough tip 122, which allows light traversing through the flexible fiber optic tip member 100 to diffuse. The flexible fiber optic tip member 100 has a polymer core along with a proximal end 110 configured for coupling to the light source 300 and a distal end 120 configured for insertion into a periodontal treatment region. The flexible fiber optic tip member 100 is configured to have a conical portion 140 proximal to a cylindrical portion 150. The cylindrical portion 150 can be configured to comprise a ridge 160 proximal to a flexible portion 170 which terminates at the distal end 120. The distal portion of flexible portion 170 may include a rough outer surface 123 configured to allow a portion of light transmitted through the flexible portion 170 to diffuse out through the rough outer surface 123. Similarly, the distal end 120 may comprise a rough tip 122 configured to allow a portion of light transmitted through the distal end 120 to diffuse out through the rough tip 122. The flexible fiber optic tip member 100 may be grated to generate the rough outer surface 123 or the rough tip 122. The conical portion 140 may have its base at the proximal end 110. The conical portion 140 will be configured to comprise a curved structure 130 to focus the light transmitted from the light source 300 into the cylindrical portion 150. Further, the flexible fiber optic tip member 100 is configured such at that light traverses through the polymer core along the optical axis 190.

Regarding any of FIG. 2A-2D, the flexible fiber optic tip member 100 may be unitarily formed. In some embodiments, the flexible fiber optic tip member is cut from a single block of polymer material. In some embodiments, the polymer core includes polycarbonate. In some embodiments, the flexible fiber optic tip member 100 comprises polymeric materials such as, for example, any of polycarbonate, polystyrene, polyacrylate and polymethylmethacrylate materials. In some embodiments, the flexible fiber optic tip member 100 comprises glass materials such as, for example, any of quartz, silica glass, borosilicate glass, lead glass, and fluoride glass materials.

The rough outer surface 123 or rough tip 122 of the flexible fiber optic tip member 100 may be generated by any suitable method, including sandpapering and/or grating the surface of the flexible fiber optic tip member 100. The rough outer surface 123 or rough tip 122 of the flexible fiber optic tip member 100 may be generated by sandblasting techniques.

In certain embodiments, flexible fiber optic tip member 100 may be removed from phototherapeutic periodontal device and disposed of, to be replaced by a fresh flexible fiber optic tip member 100 in order to avoid cross contamination, for example, between different periodontal diseased tissue or between patients. The length of the flexible fiber optic tip member 100 may be between about 10 mm and about 30 mm. The length of the flexible fiber optic tip member 100 may be between longer than about 30 mm, and be trimmed to size by the user.

Still referring to any of FIG. 2A-2D, the curved structure 130 may be convex relative to the proximal end 110. In other words, the curved structure 130 curves toward from the light source 300, which allows the flexible fiber optic tip member 100 to focus light received from the light source 300 along the optical axis 190 for traversal along the cylindrical portion 150 of the flexible fiber optic tip member 100. Any suitable degree of curvature may be used as desired so that light is allowed to propagate and focus into the optical fiber. In some embodiments, the diameter of the proximal end 100 of the flexible fiber optic tip member is the same size as the diameter of the light source 300. In some embodiments, the diameter of the proximal end 100 of the flexible fiber optic tip member is the greater than the diameter of the light source 300, which allows the flexible fiber optic tip member 100 to prevent any light from escaping. In certain embodiments, the distance between the curved surface 130 and the light source 300 may be selected such that light from the light source 300 is focused into the fiber optic tip member 100. For example, the curved surface 130 may be touching or in minimal contact or in near proximity to the light source 300.

Still referring to any of FIG. 2A-2D, the cylindrical portion 150 of the flexible fiber optic tip member 100 may have a diameter of about 0.75-1.0 mm at its proximal end and a diameter of about 0.05-0.2 mm at its distal end 120. In some embodiments, the diameter at the distal end 120 of the flexible fiber optic tip member 100 is between about 500 micron and about 1500 micron. The cylindrical portion 150 and/or the flexible portion 170 of the flexible fiber optic tip member 100 may be sufficiently flexible so as to allow insertion of the distal end 120 into small spaces such as periodontal pockets, dental root canals, tooth cavities, oral lesions, and other hard to reach sites. The flexible fiber optic tip member 100 and, in particular, the distal end 120 may be configured to deliver and focus light directly to a periodontal treatment region to provide treatment, and/or to activate a photoactivating agent in a composition as will be described below. In certain embodiments, the flexible fiber optic tip member 100 and, in particular, the distal end 120 may be configured to disperse light in all directions and from both the distal end 120 and/or along a portion of the cylindrical portion 150 or the flexible portion 170 to aid in treatment. In some embodiments, the dispersal light in all directions is achieved by providing a rough end 122 or a rough outer surface 123, as shown in FIG. 2D.

Still referring to any of FIG. 2A-2D, the ridge 160 may be configured to be partially disposed within the distal opening 250 of the elastic tubular connecting sleeve 200. In some embodiments, the diameter of the proximal end of the ridge 160 is greater than the diameter of the distal opening 250 of the elastic tubular connecting sleeve 200. In some embodiments, the diameter of the distal end of the ridge 160 is less than the diameter of the distal opening 250 of the elastic tubular connecting sleeve 200. In some embodiments, the diameter of the ridge 160 may be between 5 mm and 10 mm.

Figure 3A:
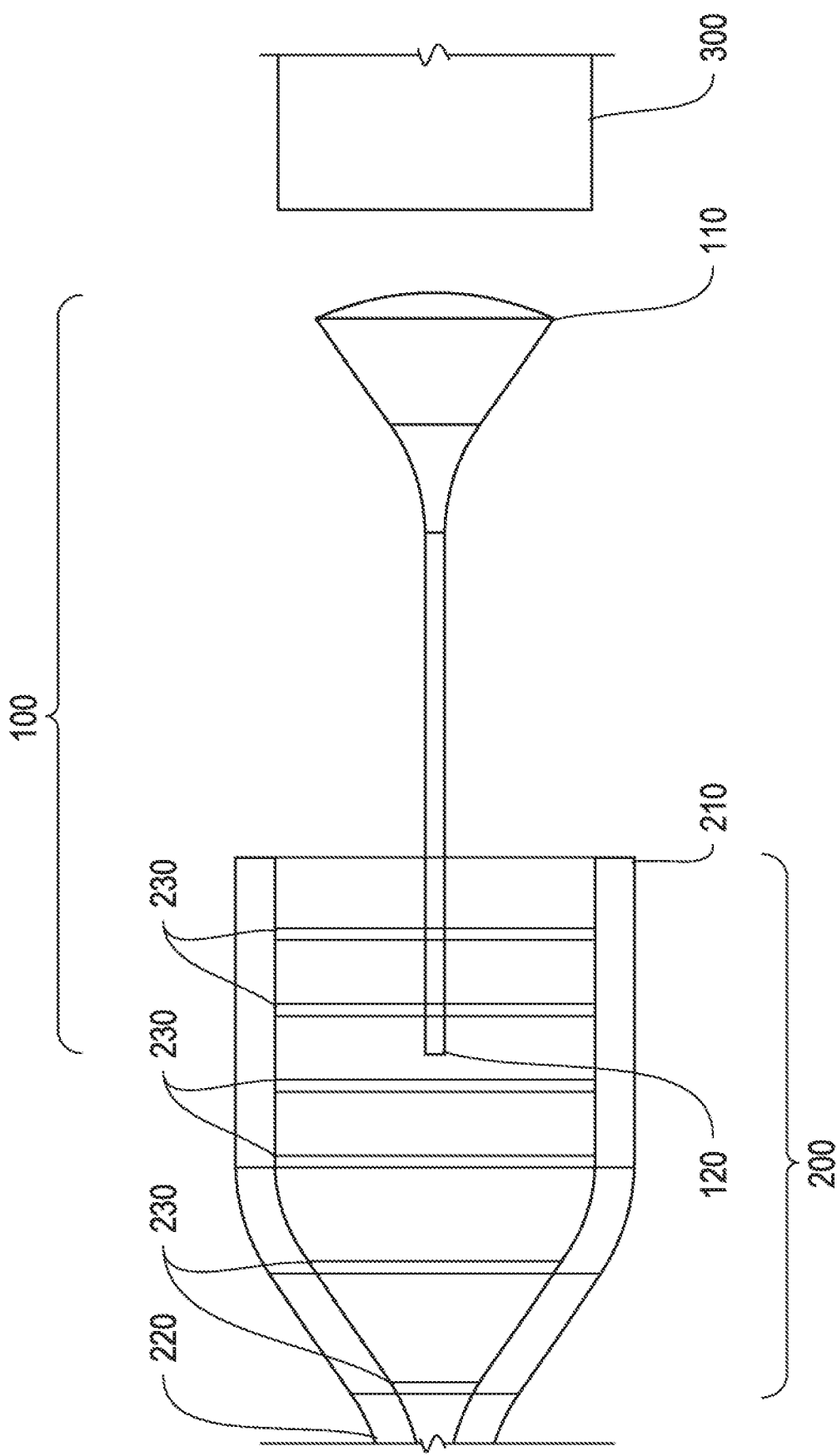
FIG. 3A depicts the coupling of the flexible fiber optic tip member to a light source using an elastic tubular connector sleeve, according to an illustrative embodiment of the present disclosure.

FIG. 3A depicts the assembly of a phototherapeutic device in accordance with the present disclosure. The proximal end 110 of the flexible fiber optic tip member 100 is coupled to the light source 300. The distal end 120 of the flexible fiber optic tip member 100 passes through the elastic tubular connector sleeve 200 and extends beyond the distal end 220 of the elastic tubular connector sleeve 200. The proximal end 210 of the elastic tubular connector sleeve 200 will extend beyond the proximal end 110 of the flexible fiber optic tip member 100 and will couple to the light source 300. The elastic tubular connector sleeve 200 will have one or more flexible ridges 230 which will allow for attachment to the light source 300 and will firmly hold the flexible fiber optic tip member 100 in place. When full assembled, the proximal end 110 of the flexible fiber optic tip member 100 will be disposed within the elastic tubular connector sleeve 200, such that the proximal end 110 of the flexible fiber optic tip member 100 is between the proximal end 210 and the distal end 220 of the elastic tubular connector sleeve 200.

Figure 3B:
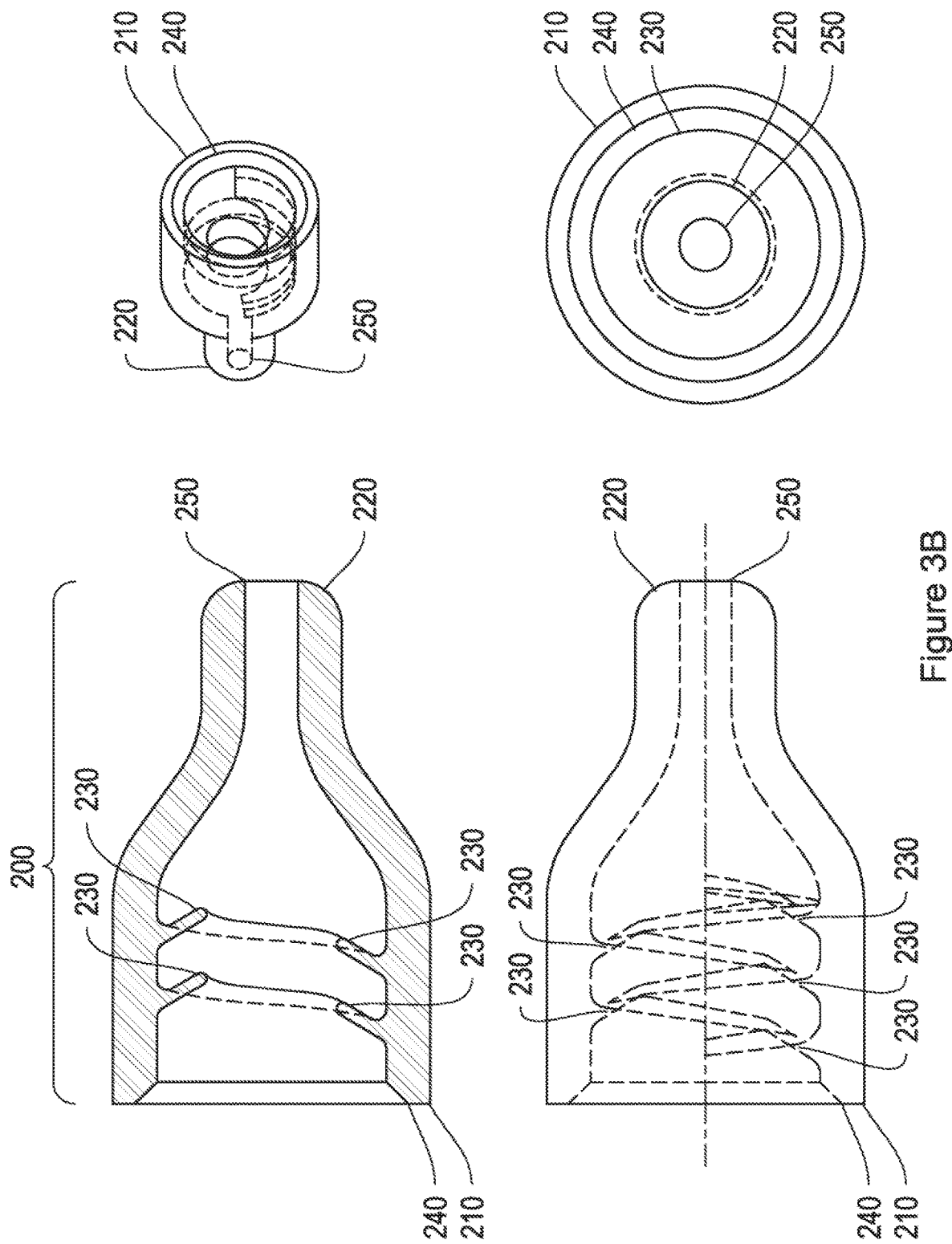
FIG. 3B depicts a zoomed-in view of an elastic tubular connector sleeve of the device of FIG. 1, according to an illustrative embodiment of the present disclosure.

FIG. 3B depicts an elastic tubular connector sleeve 200 in accordance with the present disclosure. The elastic tubular connector sleeve 200 comprises a proximal end 210, configured for coupling to a light source 300, and a distal end 220, configured to house the cylindrical portion 150 of a flexible fiber optic tip member 100. The proximal end 210 comprises a proximal opening 240 and the distal end 220 comprises a distal opening 250. A light source 300 will be coupled to the elastic tubular connector sleeve through the proximal opening 240. The cylindrical portion 150 and distal end 120 of a flexible fiber optic tip will extend through the distal opening 250. The tubular connector sleeve comprises one or more flexible ridges 230 which will allow for attachment to the light source 300 and may help hold the flexible fiber optic tip member 100 firmly in place.

The proximal end 210 of the elastic tubular connector sleeve 200 is configured for coupling to a light source 300, such that the light source 300 passes through the proximal opening 240 and is partially disposed within the elastic tubular connector sleeve 200. The proximal end 210 may be elastic, such that the diameter of the proximal opening 240 can be increased by mechanical stretching. Accordingly, the diameter of the proximal opening 240 may be the same or smaller than the diameter of the light source 300, such that the proximal end 210 must be stretched to dispose the light source 300 in the proximal opening 240. Alternatively, the proximal end 210 may be rigid, such that the diameter of the proximal opening 240 is greater than the diameter of the light source 300. In such embodiments, the one or more flexible ridges 230 keep the light source 300 partial disposed within the elastic tubular connector sleeve 200. In some embodiments, the elastic tubular connector sleeve 200 has multiple layers, including a rigid outer layer and an elastic inner layer that firmly grasps the light source 300.

The distal end 220 of the elastic tubular connector sleeve 200 is configured to allow the flexible fiber optic member 100 to extend through the distal opening 250. The distal end 220 may be configured such that the cylindrical portion 150 of the flexible fiber optic member 100 passes through the distal opening 250. Alternatively, the distal end 220 may be configured such that the conical portion 140 of the flexible fiber optic member 100 passes through the distal opening 250. In further embodiments, the distal end 220 may be configured such that the ridge 160 of the flexible fiber optic member 100 is partially disposed in the distal opening 250. In some embodiments, the distal end 220 is elastic, such that the diameter of distal opening 250 may be increased by mechanical stretching. In such embodiments, the diameter of the distal opening 250 may be the same or smaller than the diameter of the conical portion 140 or the cylindrical portion 150 of the flexible fiber optic tip member 100, such that the distal end 220 must be stretched to extend flexible fiber optic tip member 100 through the distal opening 250. Alternatively, the distal end 220 may be rigid, such that the diameter of the distal opening 250 is greater than the diameter of the conical portion 140 or the cylindrical portion 150 of the flexible fiber optic tip member 100. In such embodiments, the one or more flexible ridges 230 may keep the flexible fiber optic tip member 100 firmly disposed within the elastic tubular connector sleeve 200. Alternatively, the length of the elastic tubular connecting sleeve 200 may be short enough that when the flexible fiber optic tip member 100 is partial disposed within the connecting sleeve 200 and the connecting sleeve 200 is coupled to the light source 300, the flexible fiber optic tip 100 does not have room to move and is firmly held in place within the connecting sleeve 200. In some embodiments, the flexible fiber optic tip 100 is contacting the light source 300. In other embodiments, the flexible fiber optic tip 100 is contacting the light source 300, such as less than about 1 mm away from the light source 300.

The one or more flexible ridges 230 may be concentrically disposed within the elastic tubular connecting sleeve 200. Alternatively, the flexible ridge 230 may be a single ridge helically disposed within the elastic tubular connecting sleeve 200. The one or more flexible ridges 230 may be rigid. In such embodiments, the elastic tubular connecting sleeve 200 may be snapped onto the light source using a lip/clip method. Alternatively, the elastic tubular connecting sleeve 200 may be screwed on to the light source 300 using a threaded system. Alternatively, the one of more flexible ridges 230 may be elastic, such that the proximal end 210 of the elastic tubular connecting sleeve 200 may be mechanically stretched for coupling to the light source 300.

Figure 4:
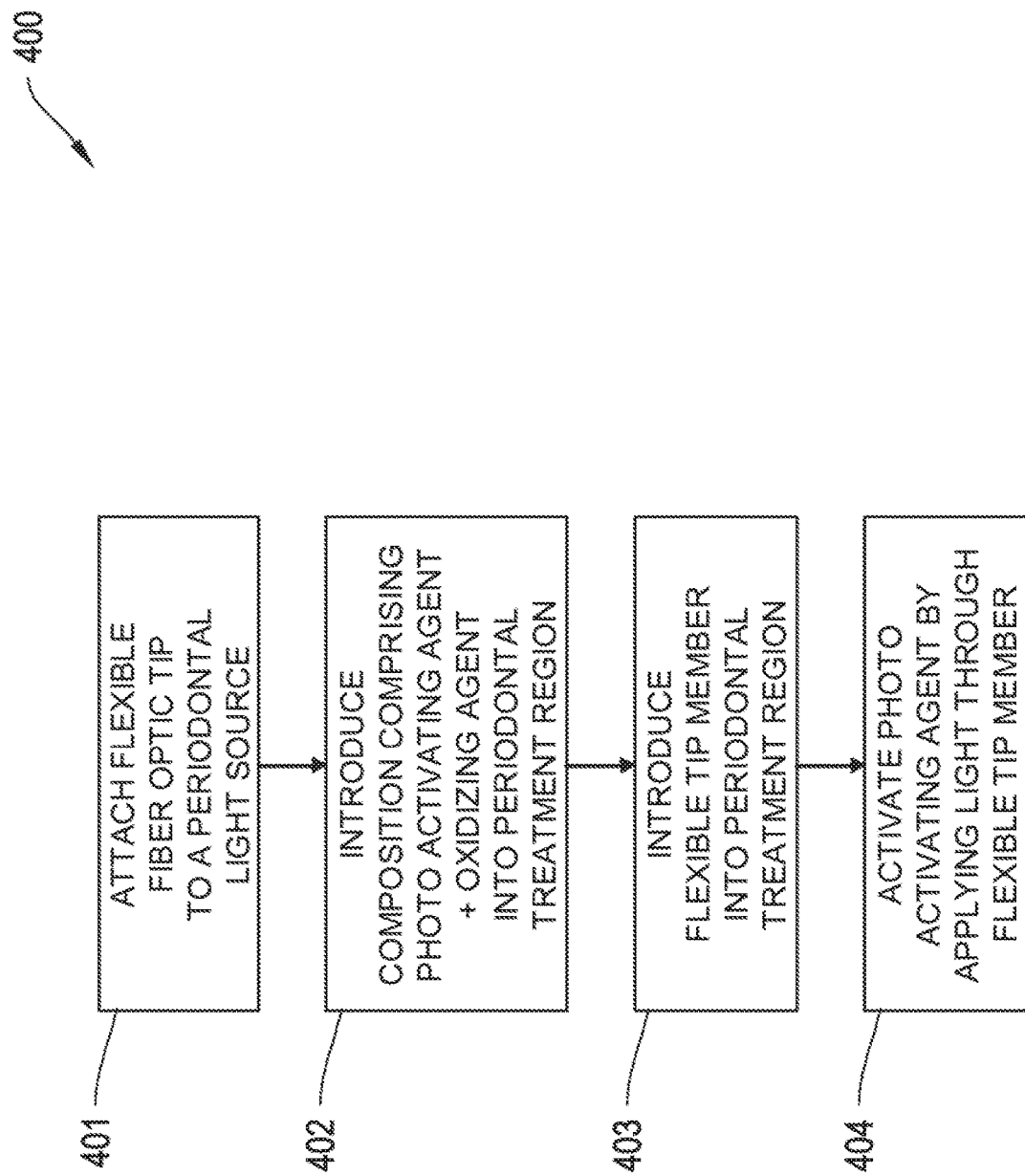
FIG. 4 is a flow chart outlining a process of treating periodontal disease using the device of FIG. 1, according to an illustrative embodiment of the present disclosure.

FIG. 4 depicts a process of treating or preventing periodontal disease 400 in accordance with the present disclosure. The process 400 comprises an attachment 401, wherein a flexible fiber optic tip 100 is attached to a periodontal light source 300 to generate a phototherapeutic device. Preferably, an elastic tubular connecting sleeve 200 is used to attach the flexible fiber optic tip 100 to the light source 300, as shown in FIG. 1 and FIG. 3A. The process 400 further comprises a composition introduction 402, wherein a composition comprising a photoactivating agent and optionally an oxygen-releasing agent is introduced into a periodontal treatment region. The process 400 further comprises a flexible tip member introduction 403, wherein the flexible fiber optic tip member 100 of the phototherapeutic device is inserted into the periodontal treatment region. The process 400 further comprises an activation 404, wherein light from the flexible fiber optic tip member 100 activates the photoactivating agent.

In one example, upon activation with light from the flexible fiber optic tip 100, the photoactivating agent absorbs energy from the light and releases some of the absorbed light energy as a fluorescent light. Without being bound to theory, it is thought that fluorescent light emitted by photoactivated chromophores may have therapeutic properties due to its femto-second or pico-second emission properties which may be recognized by biological cells and tissues, leading to favourable biomodulation. Furthermore, the emitted fluorescent light has a longer wavelength and hence a deeper penetration into the tissue than the activating light. Irradiating tissue with such a broad range of wavelength, including in some embodiments the activating light which passes through the composition, may have different and complementary therapeutic effects on the cells and tissues.

In another example, the composition also comprises an oxygen-releasing agent. In this case, the photoactivating agent may transfer at least some of the absorbed light energy to the oxygen-releasing agent, which in turn can produce oxygen radicals such as singlet oxygen. These are distinct applications of these agents and differs from the use of chromophores as simple stains or as a catalyst for photopolymerization.

Suitable photoactivating agents include fluorescent dyes (or stains), biological dyes, histological dyes, food colorings, naturally occurring photoactive agents and carotenoids.

Suitable photoactivating agents include, but are not limited to, the following:

Chlorophyll Dyes

Exemplary chlorophyll dyes include but are not limited to chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; amphiphilic chlorophyll derivative 2, phycobiliproteins.

Xanthene Derivatives

Exemplary xanthene dyes include but are not limited to Eosin B (4',5'-dibromo,2',7'-dinitro-fluorescein, dianion); eosin Y; eosin Y (2',4',5',7'-tetrabromo-fluorescein, dianion); eosin (2',4',5',7'-tetrabromo-fluorescein, dianion); eosin (2', 4',5',7'-tetrabromo-fluorescein, dianion) methyl ester; eosin (2',4',5',7'-tetrabromo-fluorescein, monoanion) p-isopropylbenzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachloro-fluorescein, dianion); eosin; eosin dicetylpyridinium chloride ion pair; erythrosin B (2',4',5',7'-tetraiodo-fluorescein, dianion); erythrosin; erythrosin dianion; erythiosin B; fluorescein; fluorescein dianion; phloxin B (2',4',5',7'-tetrabromo-3,4,5,6-tetrachloro-fluorescein, dianion); phloxin B (tetrachloro-tetrabromo-fluorescein); phloxine B; rose bengal (3,4,5,6-tetrachloro-2',4',5',7'-tetraiodo-fluorescein, dianion); pyronin G, pyronin J, pyronin Y; Rhodamine dyes such as rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Methylene Blue Dyes

Exemplary methylene blue derivatives include but are not limited to 1-methyl methylene blue; 1,9-dimethyl methylene blue; methylene blue; methylene blue (16 .mu.M); methylene blue (14 .mu.M); methylene violet; bromomethylene violet; 4-iodomethylene violet; 1,9-dimethyl-3-dimethylamino-7-diethyl-amino-phenothiazine; and 1,9-dimethyl-3-diethylamino-7-dibutyl-amino-phenothiazine.

Azo Dyes

Exemplary azo (or diazo-) dyes include but are not limited to methyl violet, neutral red, para red (pigment red 1), amaranth (Azorubine S), Carmoisine (azorubine, food red 3, acid red 14), allura red AC (FD&C 40), tartrazine (FD&C Yellow 5), orange G (acid orange 10), Ponceau 4R (food red 7), methyl red (acid red 2), and murexide-ammonium purpurate.

In some aspects of the disclosure, the one or more photoactivating agents of the biophotonic composition disclosed herein can be independently selected from any of Acid black 1, Acid blue 22, Acid blue 93, Acid fuchsin, Acid green, Acid green 1, Acid green 5, Acid magenta, Acid orange 10, Acid red 26, Acid red 29, Acid red 44, Acid red 51, Acid red 66, Acid red 87, Acid red 91, Acid red 92, Acid red 94, Acid red 101, Acid red 103, Acid roseine, Acid rubin, Acid violet 19, Acid yellow 1, Acid yellow 9, Acid yellow 23, Acid yellow 24, Acid yellow 36, Acid yellow 73, Acid yellow S, Acridine orange, Acriflavine, Alcian blue, Alcian yellow, Alcohol soluble eosin, Allophycocyanin (APC), Alizarin, Alizarin blue 2RC, Alizarin carmine, Alizarin cyanin BBS, Alizarol cyanin R, Alizarin red S, Alizarin purpurin, Aluminon, Amido black 10B, Amidoschwarz, Aniline blue WS, Anthracene blue SWR, Auramine O, Azocannine B, Azocarmine G, Azoic diazo 5, Azoic diazo 48, Azure A, Azure B, Azure C, Basic blue 8, Basic blue 9, Basic blue 12, Basic blue 15, Basic blue 17, Basic blue 20, Basic blue 26, Basic brown 1, Basic fuchsin, Basic green 4, Basic orange 14, Basic red 2, Basic red 5, Basic red 9, Basic violet 2, Basic violet 3, Basic violet 4, Basic violet 10, Basic violet 14, Basic yellow 1, Basic yellow 2, Biebrich scarlet, Bismarck brown Y, Brilliant crystal scarlet 6R, Calcium red, Carmine, Carminic acid, Celestine blue B, China blue, Cochineal, Coelestine blue, Chrome violet CG, Chromotrope 2R, Chromoxane cyanin R, Congo corinth, Congo red, Cotton blue, Cotton red, Croceine scarlet, Crocin, Crystal ponceau 6R, Crystal violet, Dahlia, Diamond green B, Direct blue 14, Direct blue 58, Direct red, Direct red 10, Direct red 28, Direct red 80, Direct yellow 7, Eosin B, Eosin Bluish, Eosin, Eosin Y, Eosin yellowish, Eosinol, Erie garnet B, Eriochrome cyanin R, Erythrosin B, Ethyl eosin, Ethyl green, Ethyl violet, Evans blue, Fast blue B, Fast green FCF, Fast red B, Fast yellow, Fluorescein, Food green 3, Gallein, Gallamine blue, Gallocyanin, Gentian violet, Haematein, Haematine, Haematoxylin, Helio fast rubin BBL, Helvetia blue, Hematein, Hematine, Hematoxylin, Hoffman's violet, Indocyanin green, Imperial red, Ingrain blue, Ingrain blue 1, Ingrain yellow 1, INT, Kermes, Kermesic acid, Kernechtrot, Lac, Laccaic acid, Lauth's violet, Light green, Lissamine green SF, Luxol fast blue, Magenta 0, Magenta I, Magenta II, Magenta III, Malachite green, Manchester brown, Martius yellow, Merbromin, Mercurochrome, Metanil yellow, Methylene azure A, Methylene azure B, Methylene azure C, Methylene blue, Methyl blue, Methyl green, Methyl violet, Methyl violet 2B, Methyl violet 10B, Mordant blue 3, Mordant blue 10, Mordant blue 14, Mordant blue 23, Mordant blue 32, Mordant blue 45, Mordant red 3, Mordant red 11, Mordant violet 25, Mordant violet 39 Naphthol blue black, Naphthol green B, Naphthol yellow S, Natural black 1, Natural red, Natural red 3, Natural red 4, Natural red 8, Natural red 16, Natural red 25, Natural red 28, Natural yellow 6, NBT, Neutral red, New fuchsin, Niagara blue 3B, Night blue, Nile blue, Nile blue A, Nile blue oxazone, Nile blue sulphate, Nile red, Nitro BT, Nitro blue tetrazolium, Nuclear fast red, Oil red O, Orange G, Orcein, Pararosanilin, Phloxine B, Phycocyanins, Phycoerythrins. Phycoerythrin-cyanin (PEC), Phthalocyanines, Picric acid, Ponceau 2R, Ponceau 6R, Ponceau B, Ponceau de Xylidine, Ponceau S, Primula, Purpurin, Pyronin B, Pyronin G, Pyronin Y, Rhodamine B, Rosanilin, Rose bengal, Saffron, Safranin O, Scarlet R, Scarlet red, Scharlach R, Shellac, Sirius red F3B, Solochrome cyanin R, Soluble blue, Solvent black 3, Solvent blue 38, Solvent red 23, Solvent red 24, Solvent red 27, Solvent red 45, Solvent yellow 94, Spirit soluble eosin, Sudan III, Sudan IV, Sudan black B, Sulfur yellow S, Swiss blue, Tartrazine, Thioflavine S, Thioflavine T, Thionin, Toluidine blue, Toluyline red, Tropaeolin G, Trypaflavine, Trypan blue, Uranin, Victoria blue 4R, Victoria blue B, Victoria green B, Water blue I, Water soluble eosin, Xylidine ponceau, or Yellowish eosin.

In certain embodiments, the composition of the present disclosure includes any of the chromophores listed above, or a combination thereof, so as to provide a biophotonic impact at the application site. Photoactive agent compositions may increase photo-absorption by the combined dye molecules or may enhance photo-biomodulation selectivity. In some embodiments, the combination of photoactive agents may be synergistic. In some embodiments, the two or more photoactive agents are both xanthene dyes, for example, Eosin Y as a first chromophore and any one or more of Rose Bengal, Erythrosin, Phloxine B as a second chromophore. It is believed that these combinations have a synergistic effect as Eosin Y can transfer energy to Rose Bengal, Erythrosin or Phloxine B when activated. This transferred energy is then emitted as fluorescence or by production of reactive oxygen species. By means of synergistic effects of the chromophore combinations in the composition, chromophores which cannot normally be activated by an activating light (such as a blue light from an LED) can be activated through energy transfer from chromophores which are activated by the activating light. In this way, the different properties of photoactivated chromophores can be harnessed and tailored according to the cosmetic or the medical therapy required.

As discussed above, the photoactivating agent stimulates the oxygen-releasing agent in the composition to produce oxygen radicals. Bacteria are extremely sensitive to exposure to oxygen radicals, such that the production of oxygen radicals converts the composition into a bactericidal composition. Peroxide compounds are oxygen-releasing agents that contain the peroxy group (R—O—O—R), which is a chainlike structure containing two oxygen atoms, each of which is bonded to the other and a radical or some element. When a biophotonic composition of the present disclosure comprising an oxygen-releasing agent is illuminated with light, the chromophores are excited to a higher energy state. When the chromophores' electrons return to a lower energy state, they emit photons with a lower energy level, thus causing the emission of light of a longer wavelength (Stokes' shift). In the proper environment, some of this energy transfer is transferred to oxygen or the reactive hydrogen peroxide and causes the formation of oxygen radicals, such as singlet oxygen. The singlet oxygen and other reactive oxygen species generated by the activation of the biophotonic composition are thought to operate in a hormetic fashion. That is, a health beneficial effect that is brought about by the low exposure to a normally toxic stimuli (e.g. reactive oxygen), by stimulating and modulating stress response pathways in cells of the targeted tissues. Endogenous response to exogenous generated free radicals (reactive oxygen species) is modulated in increased defense capacity against the exogenous free radicals and induces acceleration of healing and regenerative processes. Furthermore, activation of the composition will also produce an antibacterial effect. The extreme sensitivity of bacteria to exposure to free radicals makes the composition of the present disclosure a de facto bactericidal composition.

Suitable oxygen-releasing agents for preparation of the active medium include, but are not limited to:

Hydrogen peroxide ($H_2O_2$) is the starting material to prepare organic peroxides. $H_2O_2$ is a powerful oxidizing agent, and the unique property of hydrogen peroxide is that it breaks down into water and oxygen and does not form any persistent, toxic residual compound. Hydrogen peroxide for use in this composition can be used in a gel, for example with 6% hydrogen peroxide. A suitable range of concentration over which hydrogen peroxide can be used in the present composition is from about 0.1% to about 6%.

Urea hydrogen peroxide (also known as urea peroxide, carbamide peroxide or percarbamide) is soluble in water and contains approximately 35% hydrogen peroxide. Carbamide peroxide for use in this composition can be used as a gel, for example with 16% carbamide peroxide that represents 5.6% hydrogen peroxide. A suitable range of concentration over which urea peroxide can be used in the present composition is from about 0.3% to about 16%. Urea peroxide brakes down to urea and hydrogen peroxide in a slow-release fashion that can be accelerated with heat or photochemical reactions. The released urea [carbamide, $(NH_2)CO_2)$], is highly soluble in water and is a powerful protein denaturant. It increases solubility of some proteins and enhances rehydration of the skin and/or mucosa.

Benzoyl peroxide consists of two benzoyl groups (benzoic acid with the H of the carboxylic acid removed) joined by a peroxide group. It is found in treatments for acne, in concentrations varying from 2.5% to 10%. The released peroxide groups are effective at killing bacteria. Benzoyl peroxide also promotes skin turnover and clearing of pores, which further contributes to decreasing bacterial counts and reduce acne. Benzoyl peroxide breaks down to benzoic acid and oxygen upon contact with skin, neither of which is toxic. A suitable range of concentration over which benzoyl peroxide can be used in the present composition is from about 2.5% to about 5%.

Specific oxygen-releasing agents that that are preferably used in the materials or methods of this disclosure include, but are not limited to hydrogen peroxide, carbamide peroxide, or benzoyl peroxide. Inclusion of other forms of peroxides (e.g. organic or inorganic peroxides) should be avoided due to their increased toxicity and their unpredictable reaction with the photodynamic energy transfer.

In certain embodiments, the photoactivating agent may be incorporated in the matrix of the flexible fiber optic tip. In this way, the flexible fiber optic tip can be made to fluoresce on activation with a light. An oxygen-releasing agent may also be included within the matrix of the flexible fiber optic tip. The concentration of the photoactive agent to be used can be selected based on the desired intensity and duration of the biophotonic activity from the flexible fiber optic tip. For example, some dyes such as xanthene dyes (e.g. Eosin Y and Fluorescein) reach a 'saturation concentration' after which further increases in concentration do not provide substantially higher emitted fluorescence. Further increasing the photoactive agent concentration above the saturation concentration can reduce the amount of activating light passing through the solid biophotonic. Therefore, if more fluorescence is required for a certain application than activating light, a high 'saturation' concentration of the photoactive agent can be used. However, if a balance is required between the emitted fluorescence and the activating light, a concentration close to or lower than the saturation concentration can be chosen.

What is claimed is:

1. A method for phototherapy, comprising:
    attaching to a light source a probe member, the probe member having a flexible fiber optic tip member with a polymer or glass core and a photoactivating agent for transmitting light, wherein the photoactivating agent is: i) within the polymer or glass core; or ii) on a surface of the polymer or glass core, and an elastic tubular connector sleeve, for mechanically coupling the flexible tip member to a light source;
    introducing the flexible tip member in a the treatment region; and
    activating the photoactivating agent by applying light through the flexible fiber optic tip member.

* * * * *